United States Patent
Pena et al.

(10) Patent No.: US 7,135,197 B2
(45) Date of Patent: Nov. 14, 2006

(54) STABLE PHARMACEUTICAL COMPOSITION USEFUL FOR TREATING GASTROINTESTINAL DISORDERS

(75) Inventors: Lorraine E. Pena, Kalamazoo, MI (US); Dennis L. Huczek, Portage, MI (US)

(73) Assignee: Pharmacia Corporation, St. Louis, MO (US)

( * ) Notice: Subject to any disclaimer, the term of this patent is extended or adjusted under 35 U.S.C. 154(b) by 524 days.

(21) Appl. No.: 10/356,915

(22) Filed: Feb. 3, 2003

(65) Prior Publication Data

US 2003/0215524 A1   Nov. 20, 2003

Related U.S. Application Data

(60) Provisional application No. 60/354,224, filed on Feb. 4, 2002.

(51) Int. Cl.
| | |
|---|---|
| *A61K 9/10* | (2006.01) |
| *A61K 31/28* | (2006.01) |
| *A61K 31/555* | (2006.01) |
| *A61K 33/24* | (2006.01) |
| *A61P 1/12* | (2006.01) |

(52) U.S. Cl. .................... 424/653; 424/604; 514/159; 514/162; 514/163; 514/164; 514/184; 514/185; 514/186; 514/503; 514/777; 514/778; 514/779; 514/780; 514/781; 514/782; 514/819; 514/925; 514/937; 514/970; 514/974; 514/975; 514/867

(58) Field of Classification Search ................ 424/653, 424/604; 514/503, 819, 970, 974, 159, 162–164, 514/184–186, 777–782, 867, 925, 937, 975
See application file for complete search history.

(56) References Cited

U.S. PATENT DOCUMENTS

| | | | |
|---|---|---|---|
| 4,801,454 A | 1/1989 | Coveney | |
| 4,940,695 A | 7/1990 | Coveney et al. | |
| 5,013,560 A | 5/1991 | Stentz et al. | |

FOREIGN PATENT DOCUMENTS

| | | |
|---|---|---|
| EP | 0 217 440 | 4/1987 |
| FR | 6197 | 4/1967 |
| FR | 2073254 | 10/1971 |
| FR | 2703250 | 7/1994 |
| GB | 1269987 | 4/1972 |

OTHER PUBLICATIONS

Nonprescription Drugs, American Pharmaceutical Association, The National Professional Society of Pharmacists, 8th Edition, 1986, pp. 73-74.

*Primary Examiner*—John Pak
(74) *Attorney, Agent, or Firm*—Linda A. Vag; Evan J. Federman

(57) ABSTRACT

The present invention provides a pharmaceutical composition comprising at least one pharmaceutically acceptable bismuth-containing compound, at least one pharmaceutically acceptable non-clay-derived suspending agent, and water. The suspension exhibits reduced upward pH drift by comparison with an otherwise similar suspension which comprises a clay-derived suspending agent. Such compositions are useful in the prevention and treatment of gastrointestinal diseases and/or disorders.

65 Claims, No Drawings

STABLE PHARMACEUTICAL COMPOSITION USEFUL FOR TREATING GASTROINTESTINAL DISORDERS

This application claims priority of U.S. provisional application Ser. No. 60/354,224 filed on Feb. 4, 2002.

FIELD OF THE INVENTION

The present invention relates to bismuth-containing pharmaceutical compositions, to methods of preparing such compositions, and to use of such compositions in treating and/or preventing gastrointestinal disorders and/or disturbances.

BACKGROUND OF THE INVENTION

Bismuth-containing pharmaceutical compositions, particularly pharmaceutical suspensions, are well known for use in treating a variety of gastrointestinal disorders including nausea, heartburn and diarrhea. Illustrative bismuth-containing suspensions currently and/or previously on the market include Pepto-Bismol® of Proctor & Gamble Company, several similar retail branded bismuth-containing suspensions (illustratively including those sold by Walgreen's®, Rite-Aid®, Spartan®, and Meijer®), and Pabizol with Paregoric of Rexall. Bismuth-containing compositions are described generally in *Handbook of Nonprescription Drugs*, 8th Edition, American Pharmaceutical Association, Washington D.C.; 1986, pages 73–74. In addition to a bismuth-containing compound, many of these products further contain, inter alia, one or more anti-microbial preservatives, magnesium aluminum silicate and other suspending agents, colorant(s), etc.

U.S. Pat. No. 4,940,695 to Coveney discloses pharmaceutical compositions suitable for oral administration comprising pharmaceutically-acceptable bismuth-containing agents, pharmaceutically-acceptable non-ionic cellulose ether polymers, and magnesium aluminum silicate.

U.S. Pat. No. 5,013,560 to Stentz discloses microbially stable liquid pharmaceutical suspensions for oral administration comprising a bismuth-containing pharmaceutical agent, benzoic acid, sorbic acid, a suspension system preferably comprising magnesium aluminum silicate, and water, wherein the suspensions have a pH within the range of about 3.0 to about 5.5.

European Patent Application No. 0 217 440 to Gonsalves discloses pharmaceutical compositions for treatment of gastrointestinal disorders comprising 1.5% to 5% of a pharmaceutically-acceptable bismuth salt, 0.3% to 1.3% magnesium aluminum silicate, 0.5% to 0.85% xanthan gum, and water, having a defined ratio of magnesium aluminum silicate to xanthan gum.

Many currently marketed bismuth-containing suspensions exhibit the undesirable characteristic of upward pH drift which is accompanied by several potential adverse consequences. For example, most pharmaceutically acceptable anti-microbial preservatives become less effective at higher pH levels. Therefore, suspensions which exhibit an increase in pH during storage more quickly reach pH levels at which one or more anti-microbial preservatives present in the suspension tend to be less effective or completely ineffective. Consequently, such suspensions more rapidly become susceptible to microbial contamination and have a relatively short shelf life. Additionally, many common pharmaceutical excipients, for example colorants such as indigo carmine and turmeric, are pH sensitive. Suspensions which exhibit pH drift and comprise pH-sensitive excipients tend to change appearance and/or color over time. Such changes are particularly undesirable from a commercial acceptance and product recognition standpoint.

It is well known that suspensions having a low pH tend to taste bitter. Since, as indicated above, many anti-microbial preservatives do not function well at higher pH's (e.g. greater than about 5), suspensions which tend to drift upward in pH must therefore be prepared at a relatively low pH in order to maintain anti-microbial effectiveness while still possessing a suitable shelf life. Consequently, such low-pH suspensions have a bitter taste and/or must utilize elaborate taste-masking systems.

Even where preservatives which are effective at high pH levels are employed, suspensions having a pH greater than about 8 are generally considered to be unpalatable. Therefore, the shelf life of a suspension which exhibits upward drift may also be limited by unpleasant taste properties at higher pH levels.

If a bismuth-containing pharmaceutical composition could be prepared which exhibits reduced upward pH drift, a significant advance in the use of bismuth-containing compositions in treating gastrointestinal disorders would result.

SUMMARY OF THE INVENTION

The present invention provides a pharmaceutical composition, preferably an orally deliverable composition in the form of a suspension, comprising at least one pharmaceutically acceptable bismuth-containing compound, at least one pharmaceutically acceptable non-clay-derived suspending agent, and water. The suspension, during storage in a closed container maintained under ambient conditions for a period of at least about 5 months, exhibits reduced upward pH drift by comparison with an otherwise similar comparative suspension that comprises at least 0.1% of a clay-derived suspending agent. Such a suspension optionally further comprises at least one pharmaceutically acceptable anti-microbial preservative.

In another embodiment, the invention provides a pharmaceutical composition, preferably an orally deliverable composition in the form of a suspension, comprising at least one pharmaceutically acceptable bismuth-containing compound, at least one pharmaceutically acceptable non-clay-derived suspending agent, and water. A suspension of this embodiment comprises zero to not more than 0.08%, preferably not more than about 0.075%, more preferably not more than about 0.06%, still more preferably not more than about 0.05%, and yet more preferably not more than about 0.04%, by weight, of a clay-derived suspending agent. In a particularly preferred embodiment, the suspension comprises substantially no amount of a clay-derived suspending agent. The suspension optionally further comprises at least one pharmaceutically acceptable anti-microbial preservative.

The term "clay-derived suspending agent" herein means any suspending agent which occurs in and/or is extracted from clay, including such suspending agents in natural, purified, refined and/or synthetic form. Non-limiting illustrative examples of clay-derived suspending agents include magnesium aluminum silicate, bentonite, kaolin, etc. A "non-clay-derived suspending agent" herein includes, without limitation, all suspending agents which are not clay-derived suspending agents. The term "pharmaceutically acceptable" herein means suitable for oral administration to a human subject or non-human animal.

DETAILED DESCRIPTION OF THE INVENTION

Pharmaceutically Acceptable Bismuth-containing Compound

Compositions of the present invention comprise at least one pharmaceutically acceptable bismuth-containing compound, preferably in the form of a salt. Such bismuth-containing compounds illustratively include bismuth aluminate, bismuth subcarbonate, bismuth subcitrate, bismuth nitrate, bismuth citrate, tripotassium dicitrato bismuthate, bismuth subgallate, bismuth subnitrate, bismuth tartrate, bismuth subsalicylate and mixtures thereof. Bismuth subsalicylate is a particularly preferred bismuth-containing compound.

Compositions of the present invention typically comprise at least one pharmaceutically acceptable bismuth-containing compound in a total amount of about 0.01% to about 50%, preferably about 0.05% to about 25%, more preferably about 0.1% to about 10%, and still more preferably about 0.5% to about 5%, by weight.

Pharmaceutically Acceptable Non-clay-derived Suspending Agent

Compositions of the present invention comprise at least one pharmaceutically acceptable non-clay-derived suspending agent. Such non-clay-derived suspending agents can be inorganic or organic, cellulosic or non-cellulosic, and/or polymeric or non-polymeric. One illustrative class of non-clay-derived suspending agents includes polymers, for example cellulosic and non-cellulosic polymers. Cellulosic polymers are a particularly preferred group of non-clay-derived suspending agents. Non-limiting examples of suitable cellulosic polymers include methylcellulose, hydroxypropylmethylcellulose, hydroxybutylmethylcellulose, hydroxyethylmethylcellulose, ethylhydroxyethylcellulose, hydroxyethylcellulose, hydroxypropylcellulose, carboxymethylcellulose sodium, microcrystalline cellulose, a combination of carboxymethylcellulose sodium and microcrystalline cellulose (e.g. Avicel RC-591 of FMC Corp.), and mixtures thereof.

Particularly preferred suspending agents include carboxymethylcellulose sodium, microcrystalline cellulose, a combination of carboxymethylcellulose sodium and microcrystalline cellulose, xanthan gum, silicon dioxide, and mixtures thereof.

At least one pharmaceutically acceptable non-clay-derived suspending agent is present in a composition of the invention in a total amount of about 0.01% to about 15%, preferably about 0.05% to about 10%, and more preferably about 0.1% to about 5%, by weight. It will be understood that at least one pharmaceutically acceptable suspending agent will be selected, by type and amount, so as to create a suspension exhibiting acceptable flow properties and substantially no phase separation upon standing.

Pharmaceutically Acceptable Anti-microbial Preservative

In a preferred embodiment, a composition of the invention comprises at least one pharmaceutically acceptable anti-microbial preservative. Non-limiting examples of anti-microbial preservatives include butylparaben, editic acid, ethylparaben, glycerol, methylparaben, potassium sorbate, propionic acid, propylene glycol, propylparaben, salicylic acid, sorbic acid, sodium benzoate, sodium propionate, sodium salicylate, etc. Presently preferred anti-microbial preservatives include sorbic acid, benzoic acid, methylparaben, salicylic acid, and sodium salicylate, and salts thereof.

If desired, one or more pharmaceutically acceptable anti-microbial preservatives are present in a composition of the invention in a total amount, by weight, of about 0.01% to about 10%, preferably about 0.01% to about 5%, and more preferably about 0.01% to about 2.5%.

Initial pH and pH Stability

A presently contemplated advantage of compositions of the invention is that they exhibit little or no upward pH drift by comparison with currently marketed bismuth-containing suspensions. The term "upward pH drift" herein refers to an increase in pH, relative to pH measured immediately after preparation, of a suspension during storage in a closed container maintained under ambient conditions for a period of time. A composition of the invention preferably has a pH, measured immediately after preparation, which is acceptable for oral administration, for example to a human subject. In general, a suspension having a pH of about 2 to about 8 is considered acceptable for oral administration to a human subject. Preferably, a composition of the invention has a pH, measured immediately after preparation, of about 3 to about 7, and more preferably about 3.5 to about 6.

During storage of a composition of the invention in a closed container maintained under ambient conditions for a period of at least about 5 months, more preferably at least about 7 months, still more preferably at least about 10 months, yet more preferably at least about 12 months, and even more preferably at least about 24 months, the composition preferably exhibits an increase in pH of zero to not more than about 0.6, preferably not more than about 0.4, still more preferably not more than about 0.3, yet more preferably not more than about 0.2, and even more preferably not more than about 0.1.

In a particularly preferred embodiment, a composition of the invention, during storage in a closed container maintained under ambient conditions for a period of at least about 5 months, preferably at least about 7 months, more preferably at least about 10 months, still more preferably at least about 12 months, yet more preferably at least about 16 months, and even more preferably at least about 24 months, exhibits substantially no increase in pH.

In another embodiment, a composition of the invention, during storage in a closed container maintained under ambient conditions over a period of not less than about 5 months, preferably not less than about 7 months, more preferably not less than about 10 months, still more preferably not less than about 12 months, yet more preferably not less than about 16 months, and even more preferably not less than about 24 months, exhibits an average increase in pH during the storage period of zero to not more than about 0.06/month, preferably not more than about 0.025/month, more preferably not more than about 0.008/month, and even more preferably not more than about 0.004/month.

In another embodiment, the invention provides an orally deliverable suspension comprising at least one pharmaceutically acceptable bismuth-containing compound, at least one pharmaceutically acceptable non-clay-derived suspending agent, and water. A suspension of this embodiment comprises zero to not more than about 0.08%, preferably not more than about 0.075%, more preferably not more than about 0.06%, still more preferably not more than about 0.05%, and yet more preferably not more than about 0.04%, by weight, of a clay-derived suspending agent and, during storage in a closed container maintained under ambient conditions for a period of at least about 5 months, preferably at least about 10 months, more preferably at least about 12 months, yet more preferably at least about 16 months and still more preferably at least about 24 months, the suspension exhibits reduced upward pH drift by comparison with an otherwise similar comparative composition wherein the at least one non-clay-derived suspending agent is replaced by a clay-derived suspending agent, for example magnesium aluminum silicate. Such a composition preferably further comprises at least one pharmaceutically acceptable antimicrobial preservative.

Water

Compositions of the invention preferably comprise about 50% to 99%, preferably about 60% to about 95%, and more preferably about 65% to about 92.5%, by weight, water.

Anti-foaming Agent

Compositions of the invention optionally comprise at least one anti-foaming agent. Without being bound by theory, it is believed that an anti-foaming agent present in a composition of the invention can reduce intestinal gas experienced by a subject ingesting such a composition and/or limit foaming during preparation and/or processing of a composition of the invention. Silicone-based polymers are preferred antifoaming agents. Non-limiting examples of suitable anti-foaming agents include polydimethylsiloxane (e.g. simethicone USP), 7-9245 30% simethicone emulsion of Dow Corning, Sigma Antifoam A Concentrate, and dimethicone (e.g. FG-10 anti-foam emulsion of Dow Corning). If desired, at least one anti-foaming agent is present in a composition of the invention in a total amount, by weight, of about 0.0001% to about 5%, preferably about 0.0005% to about 4%, and more preferably about 0.001% to about 2.5%.

Additional Excipients

Compositions of the invention can comprise any additional pharmaceutically acceptable excipients. The term "excipient" herein means any substance, not itself a therapeutic agent, used as a carrier or vehicle for delivery of a therapeutic agent to a subject or added to a pharmaceutical composition to improve its handling, storage, consistency, flow properties, appearance, disintegration, dispersion, dissolution, release or organoleptic properties or to permit or facilitate formation of a dose unit of the composition into a discrete article such as a capsule suitable for oral administration. Excipients can include, by way of illustration and not limitation, diluents, buffers, substances added to mask or counteract a disagreeable taste or odor, flavors, dyes, preservatives, fragrances, and substances added to improve appearance of the composition.

Dosage Forms

A composition of the invention is preferably in the form of liquid, preferably an orally deliverable liquid, and more preferably an imbibable suspension having a viscosity suitable for pouring and oral ingestion. Preferably, where the composition is in the form of an imbibable suspension, such a suspension has a Brookfield viscosity of about 100 to about 5000 cP, more preferably about 200 to about 4000 cP, and still more preferably about 300 to about 3000. Particularly preferably, such a suspension exhibits substantially no phase separation upon standing under ambient conditions for a period of at least about 5 days, preferably at least about 20 days, more preferably at least about 30 days, and still more preferably at least about 60 days.

In another embodiment, a composition of the invention is in the form of a discrete dosage unit, for example a suspension enclosed by a capsule. Compositions of the invention can be prepared by any suitable process, not limited to processes described herein.

Utility of Compositions of the Invention

Compositions of the invention are useful in the treatment of gastrointestinal disorders and/or disturbances. The term "gastrointestinal disorders and/or disturbances" herein includes any disease, disorder or disturbance of the gastrointestinal tract which is treatable or preventable by oral administration of a bismuth-containing compound. Such disturbances are well known and include, for example, diarrhea including travelers diarrhea, nausea, vomiting, heartburn, indigestion, upset stomach, and treatment and/or prevention of gastritis and ulcers, particularly when *Campylobacter pylori* or *Helicobacter pylori* infection is present.

In treatment of gastrointestinal disorders and/or disturbances, a subject will ingest a safe and effective amount of a composition of the invention. Such a safe and effective amount will depend on, inter alia, the condition being treated, the particular bismuth-containing compound(s) present in the composition, and the age, weight and general health of the subject being treated.

Typically, a composition of the invention will be administered in a therapeutically effective daily amount of about 10 mg to about 500 g. Such a composition can be administered one or more times per day. Preferably a composition of the invention is administered not more than about 15 times per day, and more preferably not more than about 10 times per day. Generally, an amount of a composition of the invention sufficient to provide a subject with a therapeutically effective daily dose is an amount which provides the subject with at least one bismuth-containing compound in a total amount of about 5 mg to about 10,000 mg, preferably about 50 mg to about 8,500 mg, more preferably about 100 mg to about 6,000 mg.

EXAMPLES

The following examples are for illustrative purposes only and are not to be construed as limitations.

Example 1

Two suspensions, SS1 and SS2, were prepared comprising, on a % weight basis, bismuth subsalicylate (1.746%), salicylic acid (0.122%) and sodium salicylate (0.4%). SS1 comprised no magnesium aluminum silicate while SS2 further comprised 2.0% magnesium aluminum silicate. The suspensions were stored in a closed container maintained under ambient conditions for a period of 20 months, during which time samples from each suspension were drawn and pH measurements were taken. Data are shown in Table 1.

TABLE 1

| pH change in suspensions SS1 and SS2 over time | | | | | |
| --- | --- | --- | --- | --- | --- |
| Suspension | Initial pH | 1 month pH | 4 month pH | 9 month pH | 20 month pH |
| SS1 | 3.52 | 3.70 | 3.88 | 3.93 | 3.99 |
| SS2 | 4.27 | 5.68 | 5.86 | 6.24 | 6.52 |

These data show that the presence of magnesium aluminum silicate in a suspension results in the suspension having a higher initial pH and exhibiting increased upward pH drift over time compared to a similar suspension without magnesium aluminum silicate.

Example 2

Nine suspensions, S1–S9, each having compositions shown in Table 2, were prepared according to the following general procedure. Purified water was weighed, placed in a vessel, and heated to 40° C. Salicylic acid (if present in the suspension) was dissolved in the water with stirring. One or more preservatives, if present, and sucrose were added to the water with stirring. One or more suspending agents were dry blended and slowly added to the water to form a suspension and the suspension was mixed for ten minutes. Bismuth subsalicylate was added to the suspension with stirring. Flavor, color and any other desired excipients were added to the suspension and the suspension was homogenized for 5 minutes. Water was added as needed. Suspension S1 comprised magnesium aluminum silicate as a suspending agent. Suspensions S2–S9 comprised no clay-derived suspending agents.

TABLE 2

Composition (% wt/vol.) of suspensions S1–S9

| Component | S1 | S2 | S3 | S4 | S5 |
|---|---|---|---|---|---|
| Bismuth subsalicylate USP | 1.746 | 1.746 | 1.746 | 1.746 | 1.746 |
| Salicylic acid USP | 0.122 | 0.122 | 0.122 | 0.122 | 0.122 |
| Sodium benzoate NF | 0.10 | 0.10 | 0.10 | 0.10 | 0.10 |
| Sorbic acid NF | 0.10 | 0.10 | 0.10 | 0.10 | 0.10 |
| Sucrose NF | 12.0 | 12.0 | 12.0 | 12.0 | 12.0 |
| Flavor | 0.15 | — | 0.05 | 0.05 | 0.05 |
| Caramel NF | 0.10 | 0.20 | 0.20 | 0.20 | 0.20 |
| Sodium salicylate USP | 0.40 | 0.40 | 0.40 | 0.40 | 0.40 |
| Xanthan gum NF | 0.50 | 0.50 | 0.50 | 0.50 | 1.0 |
| Magnesium aluminum silicate NF Type IIA | 2.0 | — | — | — | — |
| Carboxymethyl-cellulose sodium USP | — | — | 2.0 | 0.5 | — |
| Microcrystalline cellulose NF | — | — | — | — | — |
| Avicel RC-591 | — | 2.0 | — | — | — |
| Water USP | To 100 | To 100 | To 100 | To 100 | To 100 |

| Component | S6 | S7 | S8 | S9 |
|---|---|---|---|---|
| Bismuth subsalicylate USP | 1.746 | 1.746 | 1.746 | 1.746 |
| Salicylic acid USP | 0.122 | 0.122 | 0.122 | 0.122 |
| Sodium benzoate NF | 0.10 | 0.10 | 0.10 | 0.10 |
| Sorbic acid NF | 0.10 | 0.10 | 0.10 | 0.10 |
| Sucrose NF | 12.0 | 12.0 | 12.0 | 12.0 |
| Flavor | 0.15 | 0.15 | 0.15 | 0.15 |
| Caramel NF | 0.05 | 0.05 | 0.05 | 0.01 |
| Sodium salicylate USP | 0.40 | 0.40 | 0.40 | 0.40 |
| Xanthan gum NF | 0.6 | 0.75 | 0.5 | 0.5 |
| Magnesium aluminum silicate NF Type IIA | — | — | — | — |
| Carboxymethyl-cellulose sodium USP | — | — | — | — |
| Microcrystalline cellulose NF | — | — | 2.0 | 3.0 |
| Avicel RC-591 | — | — | — | — |
| Water USP | To 100 | To 100 | To 100 | To 100 |

Example 3

Suspensions S1–S9 of Example 2 were analyzed for pH drift over a period of 10–12 months. Suspension pH was measured immediately after preparation of each suspension, and then again after 10–19 months storage under ambient conditions. Data are shown in Table 3.

TABLE 3

Change in pH during storage of suspensions S1–S9

| Suspension | Initial pH | Final pH | Months stored | Total pH Increase | Average pH Increase per Month |
|---|---|---|---|---|---|
| S1 | 4.26 | 4.91 | 10 | 0.65 | 0.065 |
| S2 | 4.02 | 4.02 | 12 | 0.0 | 0.0 |
| S3 | 4.70 | 4.63 | 12 | (0.07) | (0.0058) |
| S4 | 4.25 | 4.18 | 11 | (0.07) | (0.0064) |
| S5 | 3.80 | 3.82 | 12 | 0.02 | 0.0016 |
| S6 | 3.79 | 3.82 | 12 | 0.03 | 0.0025 |
| S7 | 3.82 | 3.82 | 12 | 0.0 | 0.0 |
| S8 | 3.82 | 3.85 | 11 | 0.03 | 0.0027 |
| S9 | 3.85 | 3.87 | 11 | 0.02 | 0.0018 |

Suspension S1, comprising a clay-derived suspending agent, exhibited greater upward pH drift over a storage period of 10 months than did Suspensions S2–S9 (which comprised no clay-derived suspending agent) over storage periods of 11–12 months. Moreover, Suspension S2 exhibited no upward pH drift over a storage period of 12 months and Suspensions S3 and S4 exhibited a reduction in pH over a storage period of 12 and 11 months, respectively. Finally, after 19 months storage, Suspension S2 exhibited a pH of 4.06 (data not shown in Table 3), an increase of only 0.04 over pH of the suspension measured immediately after preparation.

Example 4

A suspension formulation, S10, was prepared according to the general procedure describe in Example 2 above. The composition of S10 is shown in Table 4.

TABLE 4

Composition (% wt/vol.) of Suspension S10

| Component | S10 |
|---|---|
| Bismuth subsalicylate USP | 3.5 |
| Salicylic acid USP | 0.122 |
| Sodium benzoate NF | 0.10 |
| Sorbic acid NF | 0.10 |
| Sucrose NF | 12.0 |
| Flavor | 0.15 |
| Caramel NF | 0.05 |
| Sodium salicylate USP | 0.40 |
| Xanthan gum NF | 0.5 |
| Avicel RC-591 | 2.0 |
| Water USP | To 100 |

Suspension S10 had a pH, measured immediately after preparation, of 4.05. After storage in a closed container maintained under ambient conditions for a period of 7 months, S10 still had a pH of 4.05.

Example 5

Two suspensions, S11 and S12, each having compositions shown in Table 5, were prepared according to the general procedure described below.

TABLE 5

Composition of (% wt/vol.) of Suspensions S11 and S12

| Component | S11 | S12 |
|---|---|---|
| Bismuth subsalicylate | 1.746 | 1.746 |
| Sorbic acid | 0.2 | 0.2 |
| Salicylic acid USP | 0.122 | 0.122 |
| Sucrose | 12 | 12 |
| Titanium dioxide | 0.4 | 0.4 |
| Avicel RC-591 | 2 | 2 |
| Xanthan gum | 0.5 | 0.5 |
| Peppermint flavor | 0.1 | 0.1 |
| FD&C Red #40 | 0.01 | 0.01 |
| Caramel | 0.1 | 0.1 |
| Sodium salicylate | 0.4 | 0.4 |
| FG-10 Antifoam (Dow) | 0.01 | — |
| Simethicone emulsion | — | 0.8 |
| Water | To 100 | To 100 |

Water was placed in a vessel and heated to 40° C. Salicylic acid, sorbic acid, and sodium salicylate were added to the water with mixing to form a solution. An anti-foaming agent was added to the solution with mixing for 10 minutes. Bismuth subsalicylate was added to the solution with mixing for 10 minutes to form a dispersion. Red coloring, titanium dioxide, flavor and caramel were added with mixing. Avicel-591 was added to the dispersion with slow mixing for 10 minutes. Sucrose and xanthan gum were slowly added to the dispersion with mixing over a period of 10 minutes to form a suspension. Water was added to the suspension as needed and the suspension was homogenized. Immediately after preparation, pH of the suspension was measured.

What is claimed is:

1. An orally deliverable liquid pharmaceutical suspension comprising:
   (a) at least one pharmaceutically acceptable bismuth-containing compound present in a total amount of about 0.1 % to about 10%, by weight;
   (b) an effective suspending amount of at least one pharmaceutically acceptable non-clay-derived suspending agent selected from the group consisting of cellulosic suspending agents, polymeric suspending agents, xanthan gum, silicon dioxide, and mixtures thereof;
   (c) at least one pharmaceutically acceptable anti-microbial preservative, wherein the preservative does not contain benzoic acid or salts thereof; and
   (d) water;
wherein during storage in a closed container maintained under ambient conditions for a period of at least about 5 months, the suspension exhibits reduced upward pH drift by comparison with an otherwise similar comparative suspension that contains at least 0.1%, by weight, of magnesium aluminum silicate.

2. The suspension of claim 1 comprising substantially no amount of a clay-derived suspending agent.

3. The suspension of claim 1 wherein the at least one pharmaceutically acceptable bismuth-containing compound is selected from the group consisting of bismuth aluminate, bismuth subcarbonate, bismuth subcitrate, bismuth nitrate, bismuth citrate, tripotassium dicitrato bismuthate, bismuth subgallate, bismuth subnitrate, bismuth tartrate, bismuth subsalicylate, and mixtures thereof.

4. The suspension of claim 1 wherein the at least one pharmaceutically acceptable bismuth-containing compound is bismuth subsalicylate.

5. The suspension of claim 1 wherein the at least one pharmaceutically acceptable bismuth-containing compound is present in a total amount of about 0.5% to about 5%, by weight.

6. The suspension of claim 1 wherein the at least one pharmaceutically acceptable non-clay-derived suspending agent is a polymer.

7. The suspension of claim 1 wherein the at least one pharmaceutically acceptable non-clay-derived suspending agent is selected from the group consisting of methylcellulose, hydroxypropylmethylcellulose, hydroxybutylmethylcellulose, hydroxyethylmethylcellulose, ethylhydroxyethylcellulose, hydroxyethylcellulose, hydroxypropylcellulose, carboxymethylcellulose sodium, microcrystalline cellulose, xanthan gum, silicon dioxide, and mixtures thereof.

8. The suspension of claim 1 wherein the non-clay-derived suspending agent is a mixture of two or more of microcrystalline cellulose, carboxymethylcellulose sodium and xanthan gum.

9. The suspension of claim 1 wherein the at least one pharmaceutically acceptable non-clay-derived suspending agent is present in a total amount of about 0.0 1% to about 15%, by weight.

10. The suspension of claim 1 wherein the at least one pharmaceutically acceptable non-clay-derived suspending agent is present in a total amount of about 0.1% to about 5%, by weight.

11. The suspension of claim 1 wherein the at least one pharmaceutically acceptable anti-microbial preservative is selected from the group consisting of butylparaben, editic acid, ethylparaben, glycerol, methylparaben, potassium sorbate, propionic acid, propylene glycol, propylparaben, salicylic acid, sorbic acid, sodium propionate, sodium salicylate, and mixtures thereof.

12. The suspension of claim 1 wherein the at least one pharmaceutically acceptable anti-microbial preservative is selected from the group consisting of sorbic acid, methylparaben, sodium salicylate, salicylic acid, and mixtures thereof.

13. The suspension of claim 1 wherein the at least one pharmaceutically acceptable anti-microbial preservative is present in a total amount of about 0.01% to about 10%, by weight.

14. The suspension of claim 1 wherein the at least one pharmaceutically acceptable anti-microbial preservative is present in a total amount of about 0.01 % to about 2.5%, by weight.

15. The suspension of claim 1 having a pH, measured immediately after preparation, of about 2 to about 8.

16. The suspension of claim 1 having a pH, measured immediately after preparation, of about 3 to about 7.

17. The suspension of claim 1 wherein, during storage in a closed container maintained under ambient conditions for a period of at least about 5 months, the suspension exhibits an upward pH drift of not more than about 0.6.

18. The suspension of claim 1 wherein, during storage in a closed container maintained under ambient conditions for a period of at least about 5 months, the suspension exhibits an upward pH drift of not more than about 0.1.

19. The suspension of claim 1 wherein, during storage in a closed container maintained under ambient conditions for a period of at least about 5 months, the suspension exhibits substantially no upward pH drift.

20. The suspension of claim 1 wherein, during storage in a closed container maintained under ambient conditions for a period of at least about 12 months, the suspension exhibits substantially no upward pH drift.

21. The suspension of claim 1 wherein the water is present in a total amount of about 50% to about 99%, by weight.

22. The suspension of claim 1 wherein the water is present in a total amount of about 65% to about 92.5%, by weight.

23. An orally deliverable liquid pharmaceutical suspension comprising:
   (a) at least one pharmaceutically acceptable bismuth-containing compound;
   (b) an effective suspending amount of at least one pharmaceutically acceptable non-clay-derived suspending agent selected from the group consisting of cellulosic suspending agents, polymeric suspending agents, xanthan gum, silicon dioxide, and mixtures thereof;
   (c) at least one pharmaceutically acceptable anti-microbial preservative, wherein the preservative does not contain benzoic acid or salts thereof; and
   (d) water;
wherein the suspension comprises zero to not more than 0.08%, by weight, of a clay-derived suspending agent and wherein the suspension has a pH, measured immediately after preparation, of about 2 to about 8.

24. The suspension of claim 23 comprising substantially no amount of a clay-derived suspending agent.

25. The suspension of claim 23 wherein the at least one pharmaceutically acceptable bismuth-containing compound is selected from the group consisting of bismuth aluminate, bismuth subcarbonate, bismuth subcitrate, bismuth nitrate, bismuth citrate, tripotassium dicitrato bismuthate, bismuth subgallate, bismuth subnitrate, bismuth tartrate, bismuth subsalicylate and mixtures thereof.

26. The suspension of claim 23 wherein the at least one pharmaceutically acceptable bismuth-containing compound is bismuth subsalicylate.

27. The suspension of claim 23 wherein the at least one pharmaceutically acceptable bismuth-containing compound is present in a total amount of about 0.01% to about 50%, by weight.

28. The suspension of claim 23 wherein the at least one pharmaceutically acceptable bismuth-containing compound is present in a total amount of about 0.5% to about 5%, by weight.

29. The suspension of claim 23 wherein the at least one pharmaceutically acceptable non-clay-derived suspending agent is a polymer.

30. The suspension of claim 23 wherein the at least one pharmaceutically acceptable non-clay-derived suspending agent is selected from the group consisting of methylcellulose, hydroxypropylmethylcellulose, hydroxybutylmethylcellulose, hydroxyethylmethylcellulose, ethylhydroxyethylcellulose, hydroxyethylcellulose, hydroxypropylcellulose, carboxymethylcellulose sodium, microcrystalline cellulose, xanthan gum, silicon dioxide, and mixtures thereof.

31. The suspension of claim 23 wherein the non-clay-derived suspending agent is a mixture of two or more of microcrystalline cellulose, carboxymethylcellulose sodium and xanthan gum.

32. The suspension of claim 23 wherein the at least one pharmaceutically acceptable non-clay-derived suspending agent is present in a total amount of about 0.01% to about 15%, by weight.

33. The suspension of claim 23 wherein the at least one pharmaceutically acceptable non-clay-derived suspending agent is present in a total amount of about 0.1% to about 5%, by weight.

34. The suspension of claim 23 wherein the at least one pharmaceutically acceptable anti-microbial preservative is selected from the group consisting of butylparaben, editic acid, ethylparaben, glycerol, methylparaben, potassium sorbate, propionic acid, propylene glycol, propylparaben, salicylic acid, sorbic acid, sodium propionate, sodium salicylate, and mixtures thereof.

35. The suspension of claim 23 wherein the at least one pharmaceutically acceptable anti-microbial preservative is selected from the group consisting of sorbic acid, methylparaben, sodium salicylate, salicylic acid, and mixtures thereof.

36. The suspension of claim 23 wherein the at least one pharmaceutically acceptable anti-microbial preservative is present in a total amount of about 0.01% to about 10%, by weight.

37. The suspension of claim 23 wherein the at least one pharmaceutically acceptable anti-microbial preservative is present in a total amount of about 0.01% to about 2.5%, by weight.

38. The suspension of claim 23 having a pH, measured immediately after preparation, of about 3 to about 7.

39. The suspension of claim 23 having a pH, measured immediately after preparation, of about 3.5 to about 6.

40. The suspension of claim 23 wherein, during storage in a closed container maintained under ambient conditions for a period of at least about 5 months, the suspension exhibits an upward pH drift of not more than about 0.6.

41. The suspension of claim 23 wherein, during storage in a closed container maintained under ambient conditions for a period of at least about 5 months, the suspension exhibits an upward pH drift of not more than about 0.1.

42. The suspension of claim 23 wherein, during storage in a closed container maintained under ambient conditions for a period of at least about 5 months, the suspension exhibits substantially no upward pH drift.

43. The suspension of claim 23 wherein, during storage in a closed container maintained under ambient conditions for a period of at least about 12 months, the suspension exhibits substantially no upward pH.

44. The suspension of claim 23 wherein the water is present in a total amount of about 50% to about 99%, by weight.

45. The suspension of claim 23 wherein the water is present in a total amount of about 65% to about 92.5%, by weight.

46. An orally deliverable liquid pharmaceutical suspension comprising:
   (a) at least one pharmaceutically acceptable bismuth-containing compound present in a total amount of about 0.5% to about 5%, by weight;
   (b) at least one pharmaceutically acceptable non-clay-derived suspending agent selected from the group consisting of cellulosic suspending agents, polymeric suspending agents, xanthan gum, silicon dioxide, and mixtures thereof, wherein the at least one pharmaceutically acceptable non-clay-derived suspending agent is present in a total amount of about 0.1 % to about 5%, by weight;
   (c) at least one pharmaceutically acceptable anti-microbial preservative present in a total amount of about 0.01% to about 5%, by weight, wherein the preservative does not contain benzoic acid or salts thereof; and
   (d) water;
wherein the suspension comprises not more than 0.08%, by weight, of a clay-derived suspending agent and wherein the suspension has a pH, measured immediately after preparation, of about 2 to about 8.

47. The suspension of claim 46 comprising substantially no amount of a clay-derived suspending agent.

48. The suspension of claim 46 wherein the at least one pharmaceutically acceptable bismuth-containing compound is selected from the group consisting of bismuth aluminate, bismuth subcarbonate, bismuth subcitrate, bismuth nitrate, bismuth citrate, tripotassium dicitrato bismuthate, bismuth subgallate, bismuth subnitrate, bismuth tartrate, bismuth subsalicylate and mixtures thereof.

49. The suspension of claim 46 wherein the at least one pharmaceutically acceptable bismuth-containing compound is bismuth subsalicylate.

50. The suspension of claim 46 wherein the at least one pharmaceutically acceptable non-clay-derived suspending agent is a polymer.

51. The suspension of claim 46 wherein the at least one pharmaceutically acceptable non-clay-derived suspending agent is selected from the group consisting of methylcellulose, hydroxypropylmethylcellulose, hydroxybutylmethylcellulose, hydroxyethylmethylcellulose, ethylhydroxyethylcellulose, hydroxyethylcellulose, hydroxypropylcellulose, carboxymethylcellulose sodium, microcrystalline cellulose, xanthan gum, silicon dioxide, and mixtures thereof.

52. The suspension of claim 46 wherein the non-clay-derived suspending agent is a mixture of two or more of microcrystalline cellulose, carboxymethylcellulose sodium and xanthan gum.

53. The suspension of claim 46 wherein the at least one pharmaceutically acceptable anti-microbial preservative is selected from the group consisting of butylparaben, editic acid, ethylparaben, glycerol, methylparaben, potassium sorbate, propionic acid, propylene glycol, propylparaben, salicylic acid, sorbic acid, sodium propionate, sodium salicylate, and mixtures thereof.

54. The suspension of claim 46 wherein the at least one pharmaceutically acceptable anti-microbial preservative is selected from the group consisting of sorbic acid, methylparaben, sodium salicylate, salicylic acid, and mixtures thereof.

55. The suspension of claim 46 having a pH, measured immediately after preparation, of about 3 to about 7.

56. The suspension of claim 46 having a pH, measured immediately after preparation, of about 3.5 to about 6.

57. The suspension of claim 47 wherein, during storage in a closed container maintained under ambient conditions for a period of at least about 5 months, the suspension exhibits upward pH drift of not more than about 0.6.

58. The suspension of claim 47 wherein, during storage in a closed container maintained under ambient conditions for a period of at least about 5 months, the suspension exhibits upward pH drift of not more than about 0.1.

59. The suspension of claim 46 wherein, during storage in a closed container maintained under ambient conditions for a period of at least about 5 months, the suspension exhibits substantially no upward pH drift.

60. The suspension of claim 46 wherein, during storage in a closed container maintained under ambient conditions for a period of at least about 12 months, the suspension exhibits substantially no upward pH drift.

61. An orally deliverable liquid pharmaceutical suspension comprising:
  (a) at least one pharmaceutically acceptable bismuth-containing compound present in a total amount of about 0.1% to about 10%, by weight;
  (b) an effective suspending amount of at least one pharmaceutically acceptable non-clay-derived suspending agent selected from the group consisting of cellulosic suspending agents, polymeric suspending agents, xanthan gum, silicon dioxide, and mixtures thereof;
  (c) at least one pharmaceutically acceptable anti-microbial preservative, wherein the preservative does not contain benzoic acid or salts thereof; and
  (d) water;
wherein during storage in a closed container maintained under ambient conditions for a period of at least about 5 months, the suspension exhibits an average increase in pH of zero to not more than 0.06/month.

62. The suspension of claim 61 wherein during storage in a closed container maintained under ambient conditions for a period of at least about 24 months, the suspension exhibits an average increase in pH of zero to not more than 0.06/month.

63. The suspension of claim 61 wherein during storage in a closed container maintained under ambient conditions for a period of at least about 5 months, the suspension exhibits an average increase in pH of zero to not more than 0.004/month.

64. The suspension of claim 61 wherein during storage in a closed container maintained under ambient conditions for a period of at least about 24 months, the suspension exhibits an average increase in pH of zero to not more than 0.004/month.

65. A method of treating a gastrointestinal disease and/or disorder in a subject in need of such treatment, comprising oral administration to the subject of a therapeutically effective amount of a suspension of claim 1, claim 23, claim 46 or claim 61.

* * * * *